United States Patent [19]

Porsch et al.

[11] Patent Number: 4,692,243

[45] Date of Patent: Sep. 8, 1987

[54] COLUMN FOR LIQUID CHROMATOGRAPHY

[75] Inventors: Bedrich Porsch; Jaroslav Voslar; Jaroslav Rosol, all of Prague, Czechoslovakia

[73] Assignee: Ceskoslovenska akademie ved, Czechoslovakia

[21] Appl. No.: 808,234

[22] Filed: Dec. 13, 1985

Related U.S. Application Data

[63] Continuation of Ser. No. 662,695, Jun. 20, 1984, abandoned.

[30] Foreign Application Priority Data

Jun. 24, 1983 [CS] Czechoslovakia .................. 4677-83

[51] Int. Cl.$^4$ ........................................... B01D 15/08
[52] U.S. Cl. ............................................... 210/198.2
[58] Field of Search ................... 65/30.13; 210/198.2

[56] References Cited

U.S. PATENT DOCUMENTS

| 3,440,864 | 4/1969 | Blume | 210/198.2 X |
|---|---|---|---|
| 3,483,986 | 12/1969 | Wright | 210/198.2 |
| 3,615,235 | 10/1971 | Hrdina | 210/198.2 X |
| 3,763,879 | 10/1973 | Jaworek | 210/198.2 X |
| 3,771,659 | 11/1973 | Fraser | 210/198.2 |
| 3,795,535 | 3/1974 | Boller | 65/30.13 X |
| 3,816,222 | 6/1974 | Plumat et al. | 65/30.13 X |
| 3,846,100 | 11/1974 | Matsumura et al. | 65/30.13 |
| 3,855,130 | 12/1974 | Randau et al. | 210/198.2 |
| 3,878,099 | 4/1975 | Ogle | 210/198.2 |
| 3,904,527 | 9/1975 | Wilhelmson et al. | 210/198.2 |
| 3,926,800 | 12/1975 | Stephens | 210/198.2 X |
| 3,981,801 | 9/1976 | Knox | 210/198.2 X |
| 4,028,056 | 6/1977 | Snyder et al. | 210/198.2 X |
| 4,070,285 | 1/1978 | Abrahams | 210/198.2 X |
| 4,093,550 | 6/1978 | Stahl et al. | 210/198.2 |
| 4,131,547 | 12/1978 | Michel et al. | 210/198.2 |
| 4,187,177 | 2/1980 | Stahl | 210/198.2 |
| 4,246,016 | 1/1981 | Siegmond | 65/30.13 X |
| 4,280,905 | 7/1981 | Gunkel et al. | 210/198.2 |
| 4,283,280 | 8/1981 | Brownlee | 210/198.2 |
| 4,313,828 | 2/1982 | Brownlee | 210/198.2 |

FOREIGN PATENT DOCUMENTS

| 118417 | 9/1979 | Japan | 65/30.13 |
|---|---|---|---|
| 67540 | 5/1980 | Japan | 65/30.13 |

*Primary Examiner*—Robert Spitzer
*Attorney, Agent, or Firm*—Leydig, Voit & Mayer

[57] ABSTRACT

The invented column for liquid chromatography consists of a glass tube, which is inserted into a metallic tube. The metallic tube is provided with recesses in its inner wall at both ends, which accommodate conic tightening rings from metal together with conic circumferential packings from plastics, advantageously from poly(tetrafluoroethylene). The column further consists of front packings from plastics, advantageously from poly(tetrafluoroethylene, which have porous disks or filter gauzes pressed into their recesses. Both types of packing are tightened with metallic terminal elements screwed on the metallic tube, which are provided with expansion slots at sides adjacent to the front packings. The metallic tube may have openings for a visual inspection of column packing.

6 Claims, 1 Drawing Figure

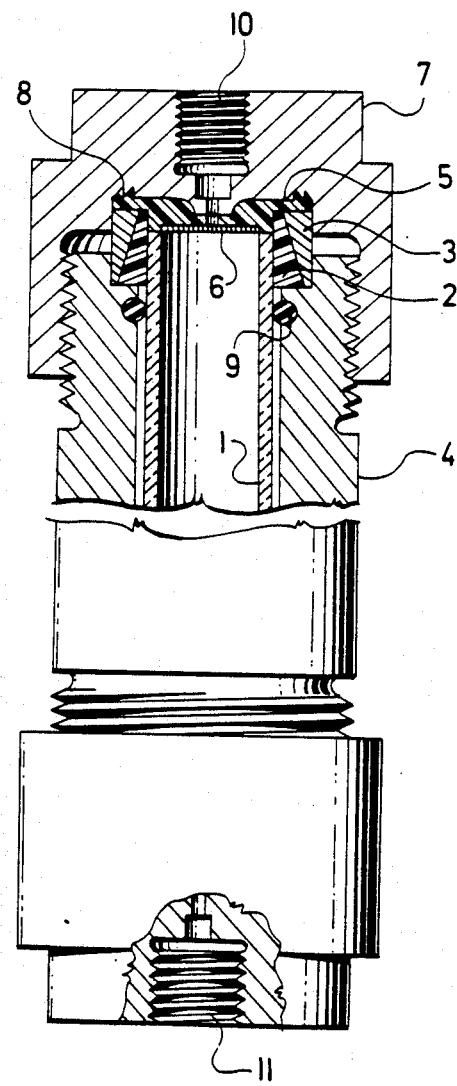

COLUMN FOR LIQUID CHROMATOGRAPHY

This is a continuation of copending application Ser. No. 662,695, filed on June 20, 1984, now abandoned.

The invention pertains to a column for liquid chromatography.

Recently, glass columns for high-pressure liquid chromatography have been developed and successfully introduced to market (Czechoslovak Patent Application PV 1635-81); the columns have the inner diameter 3.3 mm and the standard length 150 mm and are commonly used up to the pressure 50 MPa. Disadvantages of glass—a low pressure resistance and brittleness—were removed and an excellent chemical resistance of glass and a perfectly smooth inner surface were utilized. However, the columns of such diameter cannot be used for micropreparation of small fractions, because they do not allow to inject large amounts of sample (they contain only a small amount of sorbent). It is desirable to extent the inner diameter to at least 6 mm, or better to 8 mm, for this purpose. The isolation of microfractions is required for a positive identification of individual separated compounds, for example, by modern spectral methods (NMR, IR). The increased inner diameter, and thus also the inner volume, of columns is suitable also for the GPC method, in particular if the standard commercial refractometers are used.

Glass columns of larger diameter, for the modern high-pressure liquid chromatography, which are sufficiently pressure resistant, are not yet known, because a suitable construction of column, which enables to retain the pressure resistance of glass columns with a larger diameter, have not yet been designed. The columns of inner diameters 6 and 8 mm, which allow to carry out the micropreparation, are still manufactured exclusively from stainless steel. However, these columns have all shortcomings of the construction material, i.e. a low corrosion resistance in a long-termed application of, e.g., organic acids, halogenated hydrocarbons, water solutions of acids and salts. Biologically active compounds may be irreversibly changed in the contact with metal. Also the necessity of particular machining of the inner surface of stainless-steel tube should be mentioned. Those shortcomings are overcome by a glass column of larger diameter for liquid chromatography, according to the invention, a design of which secures the retention of a sufficient pressure resistance of the glass tube.

An object of the invention is a column for liquid chromatography, which consists of a glass tube placed in a metallic tube, where the metallic tube has, according to the invention, recesses in the inner wall at both ends, which accommodate, together with conic metallic tightening rings, conic circumferential packings from plastics, advantageously from poly(tetrafluoroethylene), and of front packings from plastics, advantageously from poly(tetrafluoroethylene), which carry gauzes or porous filter disks pressed into their recesses, whereas the packings are tightened with metallic terminal elements screwed on the metallic tube and the metallic terminal elements are provided, at sides adjacent to front packings, with expansion slots.

An advantage of the column according to the invention consists, above all, in an excellent chemical resistance and the perfectly smooth inner surface, which enables to achieve a high separation efficiency. Another advantage is the possible chromatography of biologic materials which do not withstand the contact with metals. The column may be readily repeatedly packed with sorbents, without some of construction elements need to be exchanged.

An advantageous performance of the column according to the invention comprises a slot below the recess in the inner wall of tube, which accommodates a rubber O-ring for centring of the glass tube. The metallic tube may have a milled slots or drilled openings for inspection of packing.

The glass tube can to be advantageously reinforced with a surface layer of potassium ions diffused into the glass at elevated temperature. This adaptation increases the tube resistance to pressure, both during packing with a sorbent and in chromatography.

The space between the glass tube and the metallic tube may be used for thermostating or for exertion an outer overpressure on the glass tube, by providing the metallic tube with an inlet of a thermostating or pressure medium. The metallic tube can be made from metals of lower corrosion resistance because it does not come into contact with mobile phases. For the same reason, the terminal element can be only lined with a corrosion-resistant central part.

The contact of separated compounds with metal can be completely excluded if suitable capillary tubes, for example, capillaries with the inner surface lined with glass, are used for the inlet and outlet of mobile phase into the column.

The column for liquid chromatography, according to the invention, is shown in the appended drawing.

The FIGURE shows a sectional view on the column according to the invention, which consists of the glass tube 1 sealed, on the one hand, with the conic packing 2 from plastics, which is inserted, together with the conic metallic tightening ring 3, into an recess in the outer carrier tube 4, and, on the other hand, with the front packing 5 from plastics, which contains the stainless-steel gauze or the porous disk 6 pressed into its recess. Both packings are tightened by the metallic terminal element 7, which has the expansion slot 8 in its inner front surface. The stainless-steel terminal elements 7 are provided with the threads 10, or also 11, for connection of the inlet and outlet of mobile phase or also of an injection equipment. The guiding rubber ring 9 may be used to achieve better centring of the glass tube.

Assembling starts with pressing the gauzes 6 into the packings 5, then the conic circumferential packing 2 and the ring 3 are inserted into the recesses in tube 4 and all parts are fixed by a moderate tightening of the terminal element 7. After assembling the sealing pieces at both ends of the column, the terminal elements 7 are tightened. The packings 2 and 5 are shaped according to the glass tube 1, which is thus sealed. At the same time, also the packing 5 is molded in such a way that it becomes fixed inside the terminal element 7, which can be then easily dismantled. The column is thus prepared for packing with a sorbent.

EXAMPLE 1

The chromatographic column was made as shown in the drawing. The glass tube from borosilicate glass (glass SIAL®) of inner diameter 5.8 mm and outer diameter 10.7 mm was 150 mm long; the outer tube 4 had the inner diameter 11 mm and wall thickness 5 mm and was made from duralumin. The conic circumferential packing 2 as well as the front packing 5 were made from poly(tetrafluoroethylene) (PTFE); the tightening ring 3 was made from stainless steel. The stainless-steel gauze of mesh diameter 3 μm was pressed into the front packing. The stainless-steel terminal elements 7 of column had openings with the threads 10 and 11 for connection of the inlet and outlet of mobile phase, or of an injection equipment. The glass tube 1 was reinforced by diffusion of potassium ions into its surface layer and resisted to the pressure 72 MPa without destruction.

EXAMPLE 2

The column was made in the same way as in Example 1 from a thick-walled glass tube 1 of length 150 mm, inner diameter 9.5 mm and outer diameter 17 mm from a borosilicate glass (SIAL ®); the outer carrying tube 4 had the inner diameter 17.5 mm and wall thickness 7 mm, was made from duralumin and had drilled openings for inspection of a packing. The column, with the glass tube 1 reinforced by diffusion of potassium ions, resisted to the pressure 72 MPa without destruction.

EXAMPLE 3

The column was made in the same way as in Example 1. The tube 1 of length 150 mm, inner diameter 9 mm and outer diameter 18 mm was from molybdenum glass; the outer tube 4 of inner diameter 18.5 mm and wall thickness 5 mm was from brass. The chemically reinforced tube 1 resisted in the column the pressure 72 MPa.

EXAMPLE 4

The column was made as in Example 1. The tube 1 from borosilicate glass (glass G-20, G.D.R.) had the inner diameter 16 mm, outer diameter 22 mm, and length 150 mm. The outer carrier tube 4 was from duralumin, had the inner diameter 16.5 mm and wall thickness 5 mm, and was provided with an inlet and outlet of thermostating liquid. The inlet and outlet also served for a pressure medium exerting a compensation overpressure during packing of the column.

We claim:

1. Column for liquid chromatography consisting of a glass tube having an inner diameter of at least 5.8 mm and a wall thickness of at least 2.45 mm, said glass tube being placed inside a metallic tube, the glass tube and the metallic tube each having a through bore, wherein the said metallic tube (4) has recesses in its inner wall at both ends, which recesses accommodate conic circumferential packings (2) from plastics, together with metallic conic tightening rings (3), and further consisting of front packings (5) from plastics, which have gauzes or porous disks (6) pressed into their recesses, and wherein the both packings are tightened with metallic terminal elements (7) screwed on the ends of tube (4), whereas the metallic terminal elements (7) are provided, at sides adjacent to the front packings (5), with expansion slots (8), whereby the circumferential packing (2), tightening ring (3) and terminal element (7), at each respective end of the metallic tube (4), co-act to seal the glass tube through bore from the metallic tube through bore, said column being characterized in that it is capable of withstanding a pressure of up to 72 MPa without destruction of the glass tube.

2. The column according to claim 1, wherein the inner wall of said metallic tube (4) is provided with a slot below the recess, which slot accommodates an elastic ring (9).

3. The column according to claim 1, wherein the terminal elements (7) are lined in the central part with a corrosion-resistant material.

4. The column according to claim 1, wherein the metallic tube (4) is provided with an inlet and an outlet for accommodating a pressure medium.

5. The column according to claim 1, wherein the glass tube (1) is reinforced by diffusion of potassium ions into the surface layer.

6. The column according to claim 1 wherein the metallic tube (4) is provided with an inlet and an outlet for accomodating a thermostating medium.

* * * * *